United States Patent [19]
Albert

[11] 3,934,005
[45] Jan. 20, 1976

[54] REDUCED SPRAY DRIFT METHOMYL COMPOSITIONS

[75] Inventor: Robert Eyer Albert, Wilmington, Del.

[73] Assignee: E. I. Du Pont de Nemours and Company, Wilmington, Del.

[22] Filed: Apr. 4, 1974

[21] Appl. No.: 457,912

[52] U.S. Cl. ............................ 424/78; 424/298
[51] Int. Cl.² ... A61K 31/74; A01N 9/06; A01N 9/20
[58] Field of Search ........ 424/78, 304, 298, 78, 304

[56] References Cited
UNITED STATES PATENTS

| | | | |
|---|---|---|---|
| 3,360,356 | 12/1967 | Vartiak | 71/65 |
| 3,576,834 | 4/1971 | Buchanun | 260/453 |

OTHER PUBLICATIONS

The Condensed Chemical Dictionary – 6th Ed. – A Rose Reinhold Publ. Corp., New York, (1964) – p. 912.
Remington's Pharm. Sciences – Hoover – Mack Publ. Co. – 13th Ed., Easton, Pa. (1965) – 1 page.

*Primary Examiner*—Albert T. Meyers
*Assistant Examiner*—D. W. Robinson

[57] ABSTRACT

Compositions of stable, concentrated, liquid methomyl formulations comprising high-molecular-weight polyoxyethylene, methomyl, and certain organic solvent systems which, when diluted with water for spray-tank use, reduce spray drift.

3 Claims, No Drawings

REDUCED SPRAY DRIFT METHOMYL COMPOSITIONS

BACKGROUND OF THE INVENTION

This invention relates to an improved method of spraying of solutions containing S-methyl-n-[(methylcarbamoyl)oxy]thioacetimidate (methomyl) insecticides. Methomyl and methomyl insecticides are described in U.S. Pat. No. 3,576,834. Methomyl insecticides are extremely effective against a wide variety of important crop insects by providing economic control at use rates of 0.25 pound or less of methomyl per acre. Liquid formulations containing high concentrations of methomyl dissolved in organic solvents are the subject of copending applications Ser. No. 317,802, filed Dec. 22, 1972, and Ser. No. 359,503, filed May 11, 1973.

Such liquid formulations are very convenient for the user. Dry powders are difficult to measure accurately by volume and the chance of accidental exposure to toxic dust is high during measuring and mixing operations. Furthermore, the solids must be dissolved in the spray tank, requiring considerable time and vigorous agitation. In liquid formulations, however, the methomyl is completely dissolved in the concentrate and the dilution to the spray concentrations is accomplished by simply adding the easily measured concentrated formulation to water in the spray tank under mild agitation conditions.

The usual method of applying dilute methomyl solutions involves spraying from as little as 1 gallon per acre to as much as 30 gallons per acre to apply the desired amount of methomyl. The higher volumes are applied with hydraulic nozzles, adjusting orifice size and fluid pressure to obtain the desired drop size range to insure complete and uniform coverage of the target. The lower volumes are applied using much smaller capacity nozzles which may utilize air or mechanical atomization to obtain a much smaller droplet size range than in the higher-volume sprays. However, regardless of the spraying technique used, a significant amount of the solution being sprayed is present as droplets much smaller than the average and desired droplet size. These very small droplets remain suspended in the air after the major portion of the spray has fallen onto the target. In the presence of even slight crosswinds, they are visible as a mist or haze moving away from the target area. This phenomena is commonly referred to as "spray drift".

Spray drift is easily carried to the surroundings adjacent to the target area, thus increasing the possibility of undesirable exposure of surroundings to toxic chemicals. In addition, these droplets, with their very high surface area per volume, evaporate to dryness very quickly and leave suspended in the air aerosol-like particles of chemical which can drift in slight winds very great distances, up to several miles or more.

It has been hypothesized that the source of the spray drift is the so-called "satellite droplets" which are usually present due to the high turbulence in and rheology of aqueous solutions issuing from small orifices. Small orifices and use of air or mechanical atomization generally increase the number of the satellite droplets formed. VanValkenburg, in "Pesticide Formulations", Marcel Mekker, Inc., New York, 1973, pp. 275-341, includes a discussion of spray drift.

Attempts to alleviate the spray-drift problem involving thickeners to increase spray solution viscosity and "particulating agents" have created other problems; for example, use of Dacagin polysaccharide gum mixture (Diamond Shamrock Corporation, 300 Union Commerce Bldg., Cleveland, OH 44114) which provides gel-like nucleii for droplet formation has resulted in difficult spray mix preparation, high pumping pressures to provide droplets in the desired size range, and nozzle plugging problems. Invert emulsions, in which the spray solution is converted to a cream-like water-in-oil emulsion in or just prior to the spray nozzle during spraying to prevent formation of the spray drift, has only very limited application to pesticides which are both water- and oil-soluble. The technique requires very close control of the two liquid streams to produce the invert emulsion, and the spray is usually comprised of very large droplets which provide insufficient coverage when spraying methomyl solutions.

More recently it has been shown that very high molecular-weight, linear, water-soluble polymers, when used in very low concentrations of 0.1 weight percent or less, significantly reduce the tendency of water- or oil-base sprays to form spray drift (U.S. Pat. No. 3,360,356). Usually, the technique involves dissolving a high-molecular-weight polymer in a portion of the water used for making up the dilute spray solution, intensely mixing until the polymer is completely dissolved, and finally adding the remaining water and pesticide while continuing to mix. Polymers dissolve very slowly, particularly with the usual type of mixing equipment used for making agricultural pesticide sprays, and mixing times up to several hours can be required. Furthermore, concentrate-solutions of the high-molecular-weight polymers are even more difficult to make and to dilute due to the extremely high-solution viscosity. If complete solution or dispersion of such high-molecular-weight polymer is not achieved, the effectiveness in reducing spray drift is decreased, and the undissolved or undispersed polymer tends to be present as gel particles which will plug nozzles, screens, and piping, resulting in spraying difficulties. It would, therefore, be very desirable to dissolve a high-molecular-weight spray-drift-reducing polymer in a liquid insecticide concentrate and then be able to easily dilute such a concentrate with water to prepare a dilute spray solution containing spray-drift-reducing agent.

U.S. Pat. No. 3,360,356 does not teach solubilities of high-molecular polymers in organic solvents, nor does it teach dissolving the polymer in a liquid insecticide concentrate for later dilution in a spray tank by the single step of adding water. Most of the almost infinite number of polymers recited in U.S. Pat. No. 3,360,356 are not soluble or dispersible in the organic solvents suitable to prepare liquid formulations of methomyl, nor is methomyl chemically stable in the presence of most of the polymers.

SUMMARY OF THE INVENTION

The invention is a single-phase, liquid methomyl concentrate composition comprising high-molecular-weight (average molecular weight greater than 1,000,000) polyoxyethylene, methomyl, and certain organic solvent systems, which can be diluted with water for spray tank use.

A suitable liquid methomyl composition consists essentially of 15–40 percent by weight of methomyl, 0.03–1.5 percent by weight of polyoxyethylene having a molecular weight of greater than one million, 0–50 percent by weight of water, and the remainder one or more low-molecular-weight, polar, organic solvents at least partially miscible with water.

For practical reasons, a preferred liquid methomyl composition consists essentially of 15–40 percent by weight of methomyl, 0.1–1 percent by weight of polyoxyethylene having a molecular weight of one million to seven million, 0–50 percent by weight of water, and the remainder one or more of the solvents selected from the group consisting of methanol, acetone, cyclohexanone, and cyclohexanol.

A most preferred liquid methomyl composition consists essentially of 20–35 percent by weight of methomyl, 0.1–1.0 percent by weight of polyoxyethylene having a molecular weight of one million to seven million, 5–40 percent by weight of water, and the remainder a solvent selected from the group consisting of methanol, mixtures of methanol and cyclohexanone, and mixtures of cyclohexanone and cyclohexanol and methanol.

DESCRIPTION OF THE INVENTION

In this invention it has been found that high-molecular-weight (greater than about 1,000,000 molecular weight average) polyoxyethylene, which is an effective spray drift control agent, can be combined with methomyl and certain solvent systems to prepare uniquely suitable concentrated liquid methomyl compositions.

The combination of solvent, methomyl, and polyoxyethylene must meet certain criteria to be useful: the compositions must have a high concentration of methomyl, 15 percent by weight or more; the methomyl must not be chemically attacked under long-term storage conditions at temperatures between about 32° and 135°F. (0° to 45°C.); the concentrated methomyl solution must be easily and quickly diluted with water to the desired spray concentration; and the applied spray must not result in injury to the target foilage or crop. In addition, it must have the required high insecticidal activity; the concentrate must remain a single-phase liquid under conditions of normal storage; the polymer must remain in solution or suspension at temperatures as low as 32°F.; and all of the formulating ingredients must meet recognizable low hazard potential during and after spray applications as defined by the Environmental Protection Agency Regulations.

Organic solvents suitable for use in high-concentration methomyl formulations containing polyoxyethylene are low-molecular-weight, polar, liquid compositions at least partially miscible in water in that the solvent will dissolve in water at spray tank concentrations. Suitable solvents dissolve at least 4% water at room temperature, and at least 4% of the solvent can be dissolved in water. Solvents which dissolve at least 6–7% water at room temperature are preferred. These liquids are also excellent solvents for both methomyl and polyoxyethylene at room temperature. Generally, low-temperature stability of the composition is enhanced if small amounts of water are included with the organic solvent. Preferred solvents are methanol, methanol-water, acetone-water, methyl ethyl ketone-water, cyclohexanone, cyclohexanone-methanol-water, cyclohexanone-cyclohexanol, cyclohexanone-cyclohexanol-water, cyclohexanol-water, and cyclohexanone-cyclohexanol-methanol-water.

Low-temperature stability without precipitation of solids or separation of liquid phases is of importance for a commodity which is shipped and stored in unheated facilities. Haze or cloudiness which occurs at low temperatures (about 30°F.) without phase separation is of little concern, since clear, uniform solutions are restored upon warming to use temperatures of 45°–50°F.

Order of addition of the ingredients during preparation of the concentrated solutions is not important. However, the preferred method is to prepare the concentrated solution of methomyl in the solvent and then slowly add the desired amount of polyoxyethylene while stirring vigorously. Agitation with mild heating, if desired, is continued until the polyoxyethylene is completely dissolved. It is preferred to adjust and maintain the pH of the concentrated methomyl solutions containing some water in the solvent system at a value of 4.5 to 5.5. A clear, nonturbid, stable solution is obtained.

Spray drift can be determined for atomizing and hydraulic spray nozzles by collecting the spray drift from the following procedures.

A. Low-Capacity, Air, or Mechanical Atomizing Nozzles

Solutions are prepared by dissolving the polyoxyethylene in a concentrated methomyl solution and a selected solvent. The polyoxyethylene content of the concentrate solution is selected so that when the concentrate is diluted with water the concentration of polyoxyethylene in the dilute solution will be more than about 0.002 weight percent but not greater than 0.05 percent by weight. 0.100 percent by weight water-soluble dye "FD&C Blue No. 1", obtained from H. Kohnstamm and Company, Incorporated, 161 Avenue of the Americas, New York, New York 10013, is then dissolved in the dilute solution.

The solution is sprayed through a DeVilbiss No. 152 atomizing nozzle obtained from the DeVilbiss Company, Somerset, Pennsylvania 15501, using atomizing air at 10 psi gauge. The spray is directed vertically downward from the nozzle, the nozzle being located so that the discharge tip is 5 inches horizontally distant from the front face of a glass fiber filter removed from a 20 inch by 10 inch by 1 inch dry "Framglas" air filter, obtained from Framm Corporation, General Products Division, P. O. Box 1637, Henderson, North Carolina 27536. The tip of the nozzle is located level with the horizontal 10-inch edge of the filter on the center line of the 20 inch by 10 inch face. The filter held in a 20 inch by 10 inch opening of a duct connected to the suction side of a fan and the fan speed adjusted so that a linear air flow speed of about 250–260 feet per minute is obtained in the plane of nozzle five inches in front of the filter. A coarse mesh screen is used to provide support on the downstream side for the filter pad. The liquid inlet of the nozzle is connected to the discharge of a "Master-Flex No. 7013" pump obtained from Cole-Parmer Co., Inc., Chicago, IL 60648, operating at 150 to 200 rpm.

The spray solution is pumped into the nozzle by immersing the tubing from the suction side of the pump into a reservoir of a known quantity of solution, and spraying is continued until considerable color is observed collecting on the screen and before liquid runoff occurs. The suction tube is removed from the reservoir, and the pumping is continued until the liquid in the tubing is completely discharged. The amount of the solution sprayed through the nozzle is determined from the reservoir.

The filter pad containing the spray drift is extracted in a weighted quantity of water of about 1-liter volume. The filter is drained, and the color of the extract is compared to previously prepared standardized solutions of the same dye in color-comparison tubes. The amount of the dye reaching the filter can now be determined and the spray drift can be calculated by comparison of dye level on the filter to total dye in the spray.

B. Spray Drift of Agricultural Nozzles

The spray drift of the solutions is determined in the same manner as for the low-capacity nozzles, except that in this case only a portion of the spray pattern is examined since the spray pattern is much larger than the 10 inch by 20 inch filter pad.

An "80015E Fan-Jet" nozzle, obtained from the Spraying Systems Co., 3201 Randolph St., Bellwood, Illinois 60104, is mounted ten inches to eighteen inches above the vertical center line of the filter pad so that the fan spray pattern is in a plane parallel to and 8 to 12 inches from the 10 inch by 20 inch front face of the pad. Preferably, in this case the 20 inch edge of the filter pad is horizontal.

Spray solutions are made up as described in Procedure A. As in Procedure A, the air velocity is adjusted to 250 to 260 feet per minute in the plane of the spray pattern and spraying is continued until the desired blue color is observed on the filter pad. Again, the quantity sprayed is determined and the spray drift from the selected portion of the spray pattern is determined. Spray drift is calculated as in procedure A.

Spray drift reduction is determined for both procedure A and B by repeating the corresponding solution example without adding the polyoxyethylene and comparing the results. Reproducibility of the spray drift reduction results are + or − 3%.

EXAMPLE 1

This example shows the effect of molecular weight of the polyoxyethylene in reducing spray drift.

Seven concentrated methomyl solutions are prepared by dissolving 25 parts by weight of technical methomyl in 67.5 parts by weight of methanol and 7.5 parts by weight of water. The pH of the solution is adjusted to 5.1 with 85% phosphoric acid. The solution is divided into seven approximately equal portions to which is added 0.9% by weight of the FD&C Blue No. 1 dye.

Into six of these concentrated solutions is dissolved 0.5 parts by weight of a Polyox polyoxyethylene polymer as indicated in the accompanying table obtained from Union Carbide Corporation, 270 Park Avenue, New York, N. Y. 10017. The remaining portion contains no polyoxyethylene.

| Solution | Commercial Designation | Polyoxyethylene Weight Average Molecular Weight |
|---|---|---|
| A | Polyox N-10 | 100,000 |
| B | Polyox N-750 | 300,000 |
| C | Polyox 1105 | 900,000 |
| D | Polyox 301 | 4,000,000 |
| E | Polyox Coagulant | 5,000,000 |
| F | Polyox FRA | >6,000,000 |
| G | None | — |

The solutions are diluted to spray concentration by diluting each with 9 parts by weight of water to 1 part by weight of the concentrate. Each solution then contains 0.05% of polyoxyethylene spray drift agent drift reduction is determined using Procedure A.

| Dilute Solution | Drift Wt. Percent | Drift Reduction Percent |
|---|---|---|
| G | 70 | 0 |
| A | 71 | 0 |
| B | 55 | 22 |
| C | 35 | 50 |
| D | 8 | 89 |
| E | 8 | 89 |
| F | 7 | 90 |

EXAMPLE 2

This example shows the effect on spray drift when spraying using an agricultural spray nozzle under normal spraying conditions. This example follows procedure B, modified as indicated below.

Solutions are sprayed through a 80015E Tee-Jet nozzle. The nozzle is mounted 10 inches above the center of the upper 10 inch horizontal edge of the filter pad and 9 inches horizontal distance from the 10 inch by 20 inch front face of the filter pad. Concentrated solutions containing polyoxyethylene are prepared as follows:

| Solution | A | B | C | D |
|---|---|---|---|---|
| Acetone, g | 313.8 | 312.50 | 314.8 | 314.51 |
| Water, g | 34.9 | 34.72 | 35.0 | 34.9 |
| Polyox 301, g | 1.40 | 2.80 | 0.28 | 0.56 |
| Weight Percent of Polyoxyethylene | 0.40 | 0.80 | 0.08 | 0.16 |

The solutions are diluted to desired spray concentration by adding appropriate amounts of water containing 0.10 percent of the No. 1 dye:

| Dilute Solution | E | F | G | H | I | J | K | M | L |
|---|---|---|---|---|---|---|---|---|---|
| Conc. Solution | None | A | B | C | D | A | B | D | C |
| Conc. Solution, g | None | 5 | 5 | 25 | 25 | 25 | 25 | 5 | 5 |
| Dyed Diluent, g | 200 | 195 | 195 | 175 | 175 | 175 | 175 | 195 | 195 |
| Dye Conc., wt. % | 0.1 | 0.0975 | 0.0975 | 0.0875 | 0.0875 | 0.0875 | 0.0875 | 0.0975 | 0.0975 |
| Polyoxyethylene, wt. % | 0.0 | 0.01 | 0.02 | 0.01 | 0.02 | 0.08 | 0.16 | 0.004 | 0.002 |
| Spray Drift, wt % | 7 | 1.3 | 0.4 | 1.2 | 0.7 | could not spray | — | 2.7 | 4.7 |
| Spray Drift Reduction, % | 0 | 81 | 94 | 83 | 90 | — | — | 62 | 34 |

The diluted solutions are sprayed through the agricultural spray nozzle at 40 PSI gauge at the nozzle. About 10% of the total fan spray is used for the drift measurement.

The effectiveness of the high molecular weight polyoxyethylene in reducing spray drift, even at very low concentration of 0.002 weight percent (20 PPM) is apparent.

EXAMPLE 3

Liquid methomyl concentrate compositions containing solvent, methomyl and Polyox 301 polyoxyethylene are prepared by dissolving the methomyl in the solvent to form a clear solution. To this solution is added slowly 0.5 percent by weight of the polyoxyethylene with vigorous stirring. solution rate is enhanced by heating to 45°C while stirring. The solutions are allowed to cool to room temperature and solution quality is observed. A portion of each solution is transfered to a small vial and sealed. The vial of each of the solutions is cooled to 32°F (0°C) and after several hours at that temperature the solution quality is again observed. Finally, the cooled solutions are allowed to warm to room temperature. Solution quality is observed. The following results were obtained (all components of the solutions are given in parts by weight of the solution and all solutions contain 0.5 percent by weight Polyox 301 polyoxyethylene).

| Solution | Methomyl Content | Solvent Composition | Content | As Made | Solution Quality At 32°F | At Room Temperature |
|---|---|---|---|---|---|---|
| 1. | 20 | Methanol | 80 | Clear | Cloudy | Clear |
| 2. | 20 | Methanol | 70 | Clear | Clear | Clear |
|    |    | Water | 10 |   |   |   |
| 3. | 20 | Cyclohexanone | 80 | Clear | Clear | Clear |
| 4. | 20 | Acetone | 70 |   |   |   |
|    |    | Water | 10 | Clear | Clear | Clear |
| 5. | 20 | Methyl Ethyl Ketone | 70 | Clear | Clear | Clear |
|    |    | Water | 10 |   |   |   |
| 6. | 20 | Cyclohexanol | 70 | Clear | Soft Gel | Clear |
|    |    | Water | 10 |   |   |   |
| 7. | 20 | Cyclohexanol | 40 |   |   |   |
|    |    | Cyclohexanone | 40 | Clear | Hazy | Clear |
| 8. | 20 | Cyclohexanol | 35 | Clear | Hazy | Clear |
|    |    | Cyclohexanone | 35 |   |   |   |
|    |    | Water | 10 |   |   |   |
| 9. | 29 | Cyclohexanone | 42 | Clear | Cloudy | Clear |
|    |    | Methanol | 8 |   |   |   |
|    |    | Water | 21 |   |   |   |
| 10. | 24 | Methanol | 68.4 | Clear | Clear | Clear |
|    |    | Water | 7.6 |   |   |   |
| 11. | 23 | Cyclohexanol | 6.9 | Clear | Clear | Clear |
|    |    | Cyclohexanone | 39.3 |   |   |   |
|    |    | Methanol | 11.6 |   |   |   |
|    |    | Coater | 19.3 |   |   |   |

The concentrated solutions are diluted with 49 parts by weight of water to 1 part by weight of the concentrate, and 0.1% by weight of the FD&C No. 1 blue dye is dissolved in each. A solution equivalent to solution 9 containing no polyoxyethylene is also prepared and diluted in a like manner and 0.1% dye dissolved in the dilute solution. This solution is designated 12.

Spray drift for each of the dilute solutions is determined as in Example 2 and determined to be:

| Dilute Solution | Spray Drift Weight Percent | Drift Reduction Percent |
|---|---|---|
| 1 | 1.42 | 80 |
| 2 | 1.28 | 82 |
| 3 | 1.21 | 83 |
| 4 | 1.35 | 81 |
| 5 | 1.42 | 80 |
| 6 | 1.35 | 81 |
| 7 | 1.21 | 83 |
| 8 | 1.35 | 81 |
| 9 | 1.28 | 82 |
| 10 | 1.35 | 81 |
| 11 | 1.42 | 80 |
| 12 | 7.10 | 0 |

I claim:

1. A single-phase liquid methomyl composition consisting essentially of 15 to 40 percent by weight of methomyl; 0.03 to 1.5 percent by weight of polyoxyethylene having a molecular weight of one million to 7 million; 0 to 50% by weight of water; and a solvent selected from the group consisting of methanol, acetone, cyclohexanone, and cyclohexanol.

2. The composition of claim 1 wherein the polyoxyethylene is 0.1 to 1% by weight of the composition.

3. A liquid methomyl composition consisting essentially of 0.1 to 1% by weight polyoxyethylene having a molecular weight of from 1 million to 7 million; 20 to 35% by weight methomyl; 5 to 40% by weight water; and a solvent selected from the group consisting of methanol, mixtures of methanol and cyclohexanone and mixtures of cyclohexanone, cyclohexanol and methanol.

* * * * *